United States Patent [19]
Cunningham

[11] Patent Number: 5,651,375
[45] Date of Patent: Jul. 29, 1997

[54] PRISONER IMMOBILIZATION DEVICE

[75] Inventor: James Cunningham, Danville, Calif.

[73] Assignee: Bio-Guardian Systems, Inc., North Platte, Nebr.

[21] Appl. No.: 735,512

[22] Filed: Oct. 23, 1996

[51] Int. Cl.$^6$ ............................................. A61B 19/00
[52] U.S. Cl. ........................... 128/869; 128/870; 128/878
[58] Field of Search ............................ 128/845, 846, 128/869, 873, 874, 875, 876; 602/19; 5/628, 631, 648

[56] References Cited

U.S. PATENT DOCUMENTS

| | | |
|---|---|---|
| 1,047,457 | 12/1912 | Steimer . |
| 2,489,828 | 11/1949 | Springer .................. 5/628 |
| 3,399,670 | 9/1968 | Veasey . |
| 3,732,863 | 5/1973 | Harrington ............... 5/628 |
| 4,004,583 | 1/1977 | Johnson . |
| 4,173,974 | 11/1979 | Belliveau . |
| 4,237,708 | 12/1980 | Bremer . |
| 4,278,553 | 7/1981 | Daniels . |
| 4,627,428 | 12/1986 | Brooks ................. 128/873 |
| 4,852,587 | 8/1989 | Share ................. 128/869 |
| 5,031,629 | 7/1991 | Wolfer ................ 128/869 |
| 5,387,185 | 2/1995 | Johnson et al. . |
| 5,400,623 | 3/1995 | Bota . |
| 5,469,813 | 11/1995 | Peden . |

OTHER PUBLICATIONS

Product Brochure "The Wrap" Safe Restraints, Inc.
Original Brochure for "The Wrap", Safe Restraints, Inc.

*Primary Examiner*—Michael A. Brown
*Attorney, Agent, or Firm*—Jones, Tullar & Cooper, P.C.

[57] ABSTRACT

A violent subject immobilization device is provided comprised of an elongated pliable trapezoidal-shaped body member of such size and shape so as to be able to be completely wrapped about the legs of a prisoner or person to be detained and extending from a position above the person's knees to a position below the person's knees. The body member has opposed outer layers of protective material and an inner unitary bendable stiffening/reinforcing material adapted to immobilize the knee joint and the wrapped leg portion of the person. Strap means are provided to permit the wrapped body member to be held in position about the legs of the person. Hand restraint means are also provided along the top edge of the body member. Upright positioning of the subject (sitting or standing) is maintained by means of a shoulder harness attachable to the body member.

13 Claims, 3 Drawing Sheets

PRISONER IMMOBILIZATION DEVICE

BACKGROUND OF THE PRESENT INVENTION

The present invention is directed to a device suitable for use by medical, paramedical and law enforcement personnel for restraining a prisoner or other person to be detained in a position which does not compromise respiratory function.

It is desirable to safely restrain persons in custody as quickly as possibly to reduce both the potential for harm to the person to be restrained as well as to the arresting officer or medical personnel. For example, handcuffs have been used to restrain hand and arm movements of the person. Other means of restraining arm movements have been employed such as devices to wrap the torso of the person. U.S. Pat. Nos. 1,047,457; 3,399,670; 4,728,553; 4,852,587; and 5,031,639 disclose various devices which have been employed to provide the desired restraint.

However, in particularly violent circumstances, the fact that the legs of the person remained unrestrained frequently results in kicking, an increased escape risk and the need to use more force than desirable to subdue the person. This occasionally results in instances of alleged police brutality and in-custody deaths due, for example, to respiratory failure. U.S. Pat. Nos. 4,004,583; 4,173,974; 4,237,708; 5,387,185; 5,400,623; and 5,469,813 disclose various means to immobilize leg movement.

It is accordingly desirable to provide a device which will enable a potentially violent person to be restrained relatively quickly while minimizing the ability of the restrained person to cause further harm either to himself or to others.

OBJECTS AND SUMMARY OF THE INVENTION

It is accordingly an object of the present invention to provide a device which may be used to restrain ankle, leg, lower torso and arm movement of a person to be detained.

It is further an object of the present invention to provide a device which may be quickly applied to the ankles and legs of a person to be detained to immobilize the ankles and knee joint and subsequent leg movement.

It is further an object of the present invention to provide a device which may be initially employed to restrain ankle movement followed by restraint of movement of the knee joint and leg movement.

In accordance with the present invention, there is thus provided a device for restraining a prisoner or other person to be restrained comprising:

(1) an elongate, pliable trapezoidal-shaped body member of such size and shape as to be able to be completely wrapped about the legs of the person to be detained, said body member extending from an upper position below the person's waist and above the knee to a lower position between the person's knee and ankle, said body member having substantially parallel opposed top and bottom edges and non-parallel opposed side edges, the distance between the opposed side edges decreasing toward the bottom of the body member;

(2) said body member comprising opposing outer layers of a protective material and an inner bendable stiffening/reinforcing material adapted to impart rigidity and to protect the wrapped leg portion of the person;

(3) at least two flexible straps sized and shaped to extend about the body member when wrapped about the legs of the person;

(4) means to secure each of said straps about said body member to maintain said body member in a wrapped position about said person's legs, said means including on at least one of said straps a snap-in buckle assembly to facilitate maintaining said body member in a wrapped position about said person's legs;

(5) hand restraint means positioned along the top edge of said body member and adapted to immobilize the wrists and hands of the person; and (6) means positioned along the upper section of said body member to permit attachment of a hand restraint device thereto.

Preferably, each of said outer material, said inner stiffening material, said strap means, said hand restraint means, said securing means and said means to permit attachment of a hand restraint device are formed of a non-metallic X-ray translucent material.

The device of the present invention further includes an adjustable strap means attached to an upper corner portion of the body member to permit the securing of handcuffed wrists behind the back of the person to be restrained. A shoulder harness is also provided which is adapted to maintain the person in an upright position without compressing the vital organs (such as kidneys) and/or inhibiting and restricting respiratory function. The shoulder harness is adjustably attached to the body member while wrapped about the legs of the person.

DETAILED DESCRIPTION OF THE PRESENT INVENTION

The restraining device of the present invention will be described in connection with the Figures.

Figure 1:
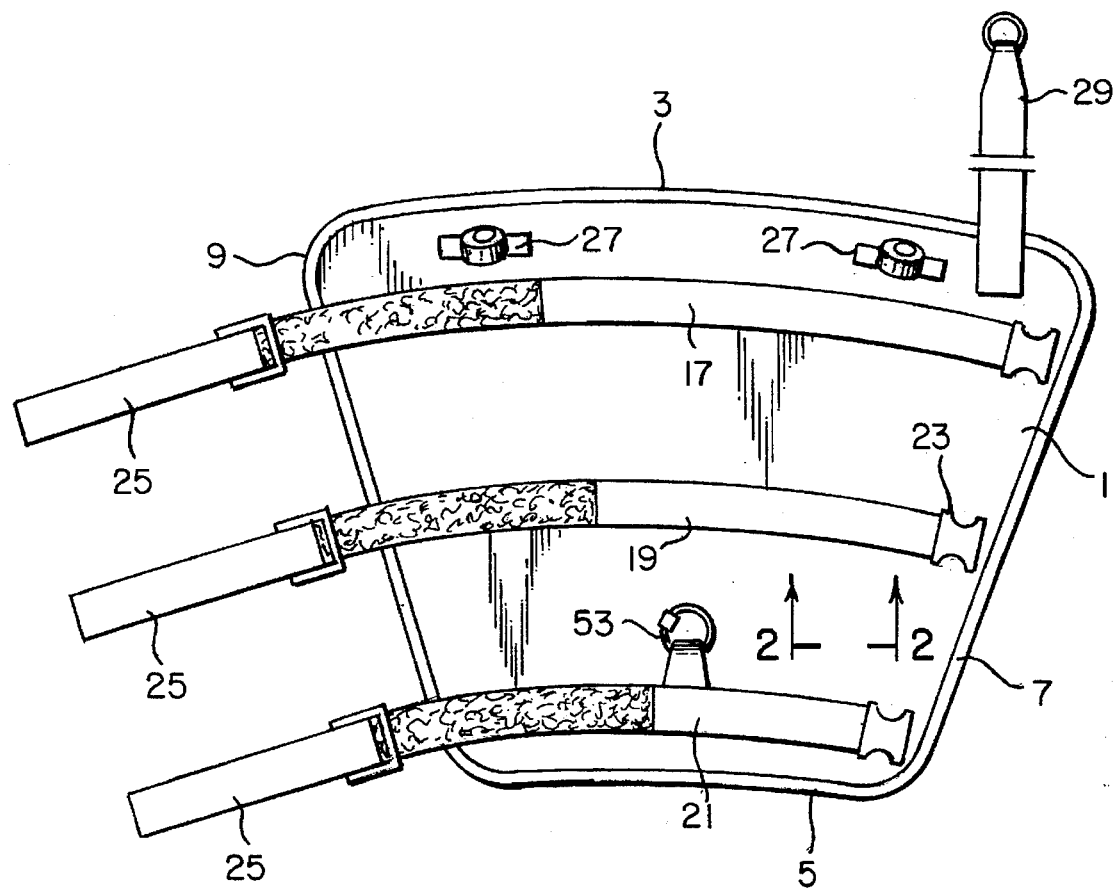
FIG. 1 is a rear elevational view of the restraining device of the present invention.

As shown in FIG. 1, the restraining device of the present invention comprises elongate body member 1 of such size and shape as to be able to be partially or completely wrapped about the legs of the person to be detained or immobilized. Body member 1 is trapezoidal-shaped in configuration, and has substantially parallel top and bottom edges 3,5 and non-parallel opposed side edges 7,9. The distance between the opposed side edges decreases toward the bottom edge of the body member in order to take into account the fact that less material is required to wrap the legs than to wrap the hip portion of the person.

The body member is sized to extend from an upper position between the person's waist and knee to a lower position between the person's knee and ankle. As a result, upon being wrapped about the person to be restrained, substantially the entirety of the person's legs may be wrapped and immobilized. By way of non-limiting example, it has been found acceptable for the width of the upper portion of the body member to be at least 38 inches, the width of the bottom portion to be at least 21 inches, and the length of the body member to be at least 26 inches for use in connection with an average size adult.

Figure 2:
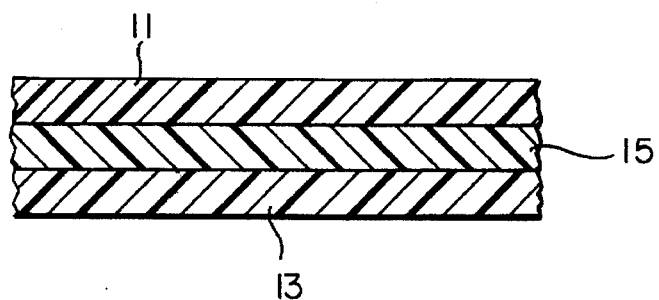
FIG. 2 is a cross-sectional view of the restraining device of FIG. 1, taken along line 2—2 of FIG. 1.

As depicted in FIG. 2, the body member comprises opposing outer layers 11,13 having an inner unitary bendable stiffening layer 15. The outer layers 11,13 are formed of a fluid-impermeable material such as a vinyl material which enables the device to be easily cleaned of dirt and body fluids that may be deposited on the device. The unitary inner layer 15 provides reinforcing/stiffening for the device. The layer 15 also serves to protect the restrained person from harm upon contact with the ground or other objects.

Layer 15 is a unitary layer which provides the necessary stiffening/reinforcement for the body member without the need for stiffening bars or rods. The inclusion of bars or rods has been found to be undesirable as the potential for injury is increased. The material employed for use as the stiffening/reinforcing layer 15 should be strong enough to resist the application of force yet flexible enough to permit the body member to be wrapped about the legs of the person to be restrained.

An exemplary material which may be used with advantage as the stiffening/reinforcement material is a tough, rigid, thermoplastic material such as an ABS (acrylonitrile-butadiene-styrene) plastic material. Such materials exhibit a desirable balance of hardness and rigidity. These materials also provide a desirable "pop-open" flex to the body member which results in the body member being caused to lay flat on the ground upon being unstrapped.

Once wrapped about the legs of the person to be restrained, the body member is held in place by straps attached to the rear portion of the body member. As shown in FIG. 1, the device includes multiple (desirably at least three) flexible straps 17, 19, 21 sized and shaped to extend about the body member and to permit attachment to maintain the body member in a wrapped position about the legs. The straps 17,19,21 preferably are positioned on the body member along an upper section of the body member, along a midsection of the body member, and along a lower portion of the body member, respectively.

Each of the straps includes means to secure the strap about the wrapped body member. At least one of the straps includes a snap-in buckle assembly 23 to facilitate connection of the strap upon the body member being wrapped about the legs of the person. Hook and loop (e.g., Velcro) fasteners 25 may be employed with advantage with the remaining straps. Alternatively, all three of the straps may include a snap-in buckle assembly as means of attachment.

Figure 4:
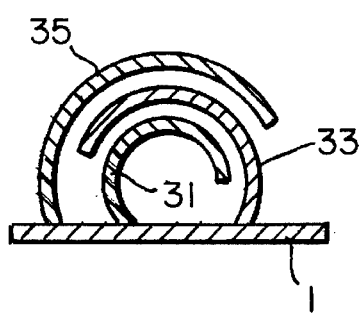
FIG. 4 is a cross-sectional view of a hand restraint assembly which may be used in the present invention.

Hand restraint means 27 are provided along the upper portion of the rear of the device. The hand restraint means may simply comprise two opposing straps of material which may be connected together (such as by hook and loop fasteners) to encompass the wrist of the person. Two of such hand restraint means are provided so that each of the hands of the person may be restrained. Desirably, as depicted in FIG. 4, the hand restraint means is comprised of multiple (i.e., two or three) straps which may cooperatively engage to provide the necessary restraint, i.e., a cushioning strap 31, a securing cushioned strap 33, and a locking strap 35, each having cooperatively engagable hook and loop fasteners on opposing surfaces to permit tight engagement of the person's wrists.

Alternatively, handcuff attachment means 29 may be provided which may be connected to a person's handcuffs to restrain movement of the person's hands. Such means 29 may simply comprise a metal ring, to which the handcuffs may be attached.

Figure 3:
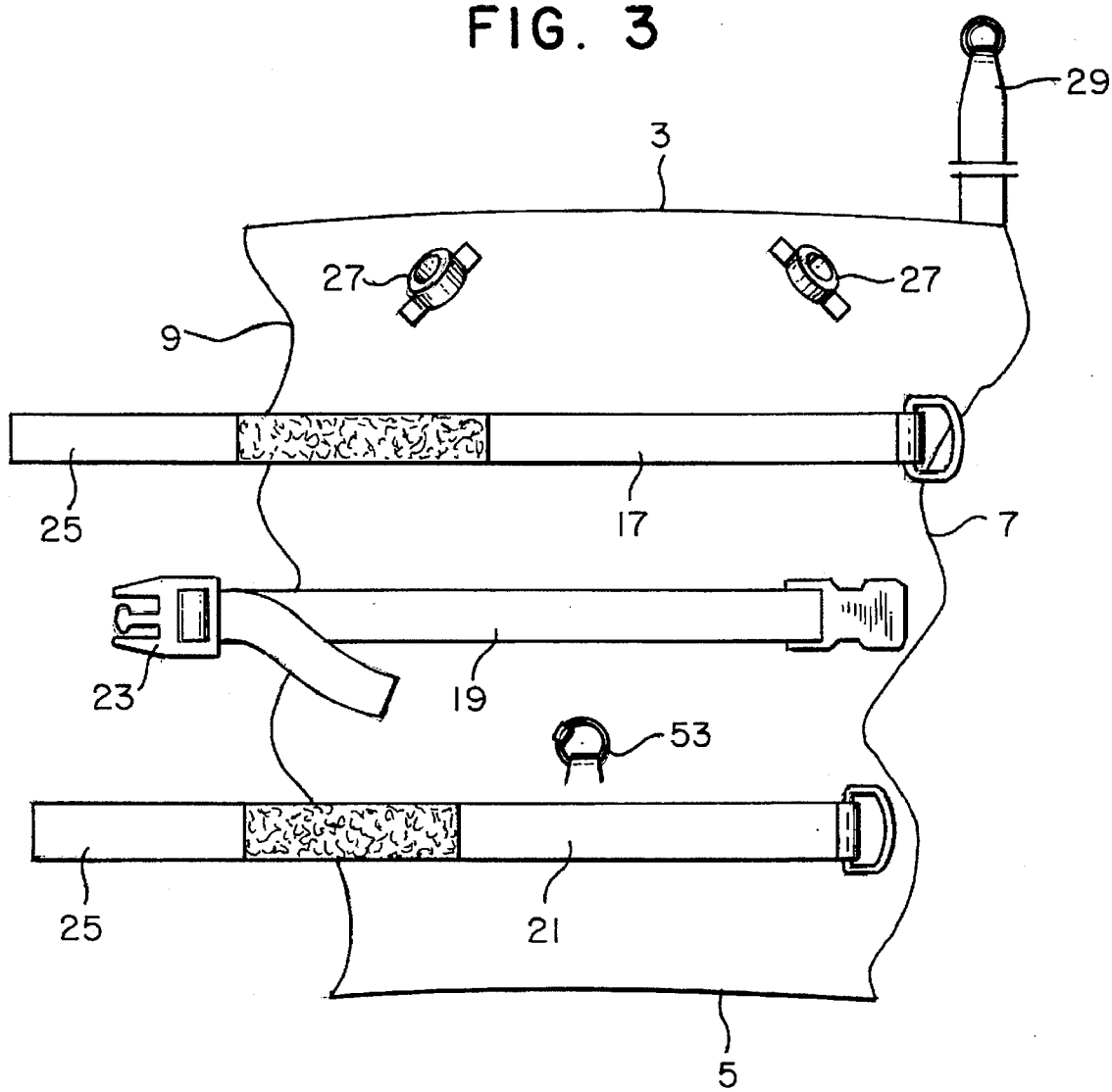
FIG. 3 is a rear elevational view of another embodiment of the restraining device of the present invention.

In a second embodiment, as depicted in FIG. 3, the opposed side edges 8, 10 of the body member are serrated or irregular in configuration and of a design so as to cooperatively mate or assist visual alignment of the body member upon wrapping of the body member about the legs of the person.

Advantageously, the device of the present invention is formed of non-metallic X-ray translucent materials. The use of such materials enables the person to also be medically examined without the need to remove the leg restraint.

Figure 5:
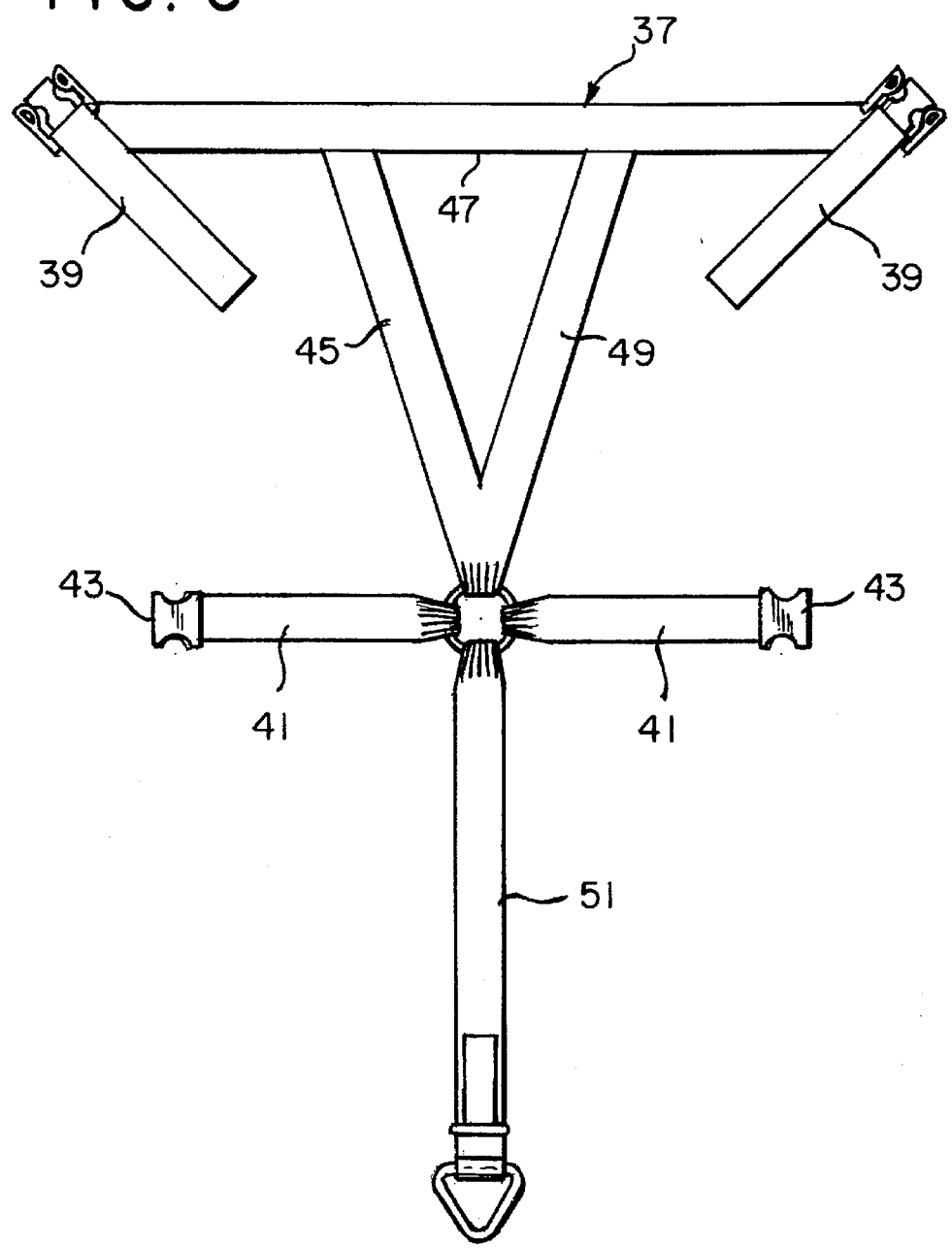
FIG. 5 is an elevational view of a shoulder harness which may be used in association with the restraining device of the present invention.

FIG. 5 depicts a shoulder harness 37 which may be employed in connection with the restraining device of FIG. 1. The shoulder harness includes opposing straps 39, 41 which may be connected via buckle means 43 around the person's shoulder and under the armpit. Tether portions 45, 47, 49 are placed over the person's head. Tether 51 may be attached by suitable means to attachment means 53 (FIG. 1) of the body member to maintain the person in an upright position. As depicted, the triangular ring at the end of tether 51 may be secured within ring 53 (FIG. 1). The length of the tether 51 is adjustable to permit the person to be maintained in an upright position and prohibited from assuming a prone position.

Figure 6:
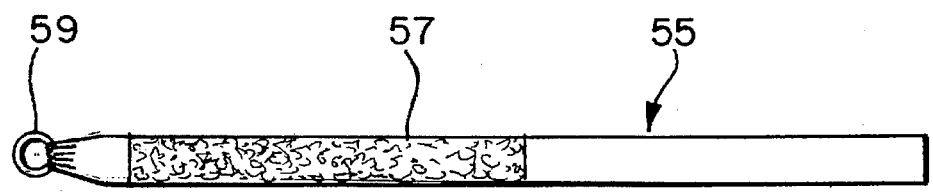
FIG. 6 is an elevational view of a strap means that may be used in conjunction with the restraining device to immobilize the ankles.

FIG. 6 depicts an ankle restraint strap 55 which may be easily wrapped about the ankles of the person to provide partial restraint prior to use of the body member to restrain the legs.

The strap means advantageously includes a hook and loop fastening portion 57 together with a ring portion 59 to permit adjustment of the strap.

In operation, the restraining device of the present invention is designed to be flat and stiff such that it can easily slide under the lower torso of the subject by handling a corner or edge of the body member to provide placement under the legs of the person to be restrained. The body member is then wrapped about the legs and held in place by means of the various strap means. The person's hands may then be immobilized either by use of the hand restraint means or by handcuffs. The person while restrained may be safely transported in an upright position upon use of the shoulder harness and connection of the harness to the restraining device via an adjustable tether from the chest area (secured by a double back strap) to the body member. The adjustable tether is pulled tight enough to prevent the person from laying prone while maintaining the person in an upright position.

What is claimed is:

1. A device for restraining a prisoner or other person to be restrained comprising:

(1) an elongate, pliable trapezoidal-shaped body member of such size and shape as to be able to be completely wrapped about the legs of the person to be detained, said body member extending from an upper position below the person's waist and above the knee to a lower position between the person's knee and ankle, said body member having substantially parallel opposed top and bottom edges and non-parallel opposed side edges, the distance between the opposed side edges decreasing toward the bottom of the body member;

(2) said body member comprising opposing outer layers of a protective material and an inner unitary bendable stiffening material adapted to immobilize the knee joint and protect the wrapped leg portion of the person;

(3) at least two flexible straps sized and shaped to extend about the body member when wrapped about the legs of the person;

(4) means to secure each of said straps about said body member to maintain said body member in a wrapped position about said person's legs, said means including on at least one of said straps a snap-in buckle assembly to facilitate maintaining said body member in a wrapped position about said person's legs;

(5) hand restraint means positioned along the top edge of said body member and adapted to immobilize the wrists and hands of the person;

(6) means positioned along the upper section of said body member to permit attachment of a hand restraint device thereto; and (7) each of said outer material, said inner stiffening material, said strap means, said hand restraint means, said securing means and said means to permit attachment of a hand restraint device being formed of an X-ray translucent material.

2. The device of claim 1 wherein said means to permit attachment of a hand restraint device extends from the top edge of said body member.

3. The device of claim 1 wherein said means to permit attachment of a hand restraint device comprises strap means.

4. The device of claim 1 wherein at least three flexible straps are employed to extend about and secure said body member.

5. The device of claim 4 wherein said three flexible straps are positioned along an upper section of said body member, a midsection of said body member and a lower section of said body member, respectively.

6. The device of claim 1 wherein each of said straps extending about said body member are secured by a snap-in buckle assembly.

7. The device of claim 1 wherein said straps extending about said body member include hook and loop securing means.

8. The device of claim 1 wherein said inner unitary stiffening material is a rigid thermoplastic material.

9. The device of claim 8 wherein said inner unitary stiffening material is an acrylonitrile-butadiene-styrene plastic material.

10. The device of claim 1 wherein said hand restraint means comprises opposing straps adapted to cooperatively engage to restrain the wrist of said person.

11. The device of claim 10 wherein said hand restraint means comprises three opposing overlapping straps which cooperatively engage to restrain the wrist of said person.

12. The device of claim 1 further including in combination a shoulder harness attached to said body member by tether means adjustable to maintain said person in an upright position while preventing said person from assuming a prone position.

13. The device of claim 1 wherein said opposed outer layers comprise a fluid-impermeable material.

* * * * *

US005651375B1

REEXAMINATION CERTIFICATE (3871st)

United States Patent [19]
Cunningham

[11] B1 5,651,375
[45] Certificate Issued Sep. 7, 1999

[54] PRISONER IMMOBILIZATION DEVICE

[75] Inventor: James Cunningham, Danville, Calif.

[73] Assignee: Bio-Guardian Systems, Inc., North Platte, Nebr.

Reexamination Request:
No. 90/004,750, Sep. 16, 1997

Reexamination Certificate for:
Patent No.: 5,651,375
Issued: Jul. 29, 1997
Appl. No.: 08/735,512
Filed: Oct. 23, 1996

[51] Int. Cl.⁶ .................................................. A61B 19/00
[52] U.S. Cl. .......................... 128/869; 128/870; 128/878

[56] References Cited

U.S. PATENT DOCUMENTS

| | | |
|---|---|---|
| 1,047,457 | 12/1912 | Steimer . |
| 2,489,828 | 11/1949 | Springer . |
| 2,766,751 | 10/1956 | Topa . |
| 2,899,692 | 9/1959 | Finken . |
| 3,933,154 | 1/1976 | Cabansag . |
| 3,947,686 | 3/1976 | Cooper et al. . |
| 4,030,719 | 6/1977 | Gabriele et al. . |
| 4,078,560 | 3/1978 | Hill . |
| 4,103,170 | 7/1978 | Spradlin . |
| 4,146,793 | 3/1979 | Bergstrom et al. . |
| 4,481,942 | 11/1984 | Duncan . |
| 4,566,445 | 1/1986 | Jelsma et al. . |
| 4,706,957 | 11/1987 | Jackson . |
| 4,742,821 | 5/1988 | Wootan . |
| 4,841,961 | 6/1989 | Burlage et al. . |
| 4,852,587 | 8/1989 | Share . |
| 4,905,267 | 2/1990 | Miller et al. . |
| 5,031,639 | 7/1991 | Wolfer . |
| 5,375,277 | 12/1994 | Carr et al. . |
| 5,533,089 | 7/1996 | Mulhern . |

OTHER PUBLICATIONS

D. Brule, "Combative Subjects Require Special Care", Jul. 1996, Police: The Law Officer's Magazine, pp. 30–31, 72.

*Primary Examiner*—Michael Anthony Brown

[57] ABSTRACT

A violent subject immobilization device is provided comprised of an elongated pliable trapezoidal-shaped body member of such size and shape so as to be able to be completely wrapped about the legs of a prisoner or person to be detained and extending from a position above the person's knees to a position below the person's knees. The body member has opposed outer layers of protective material and an inner unitary bendable stiffening/reinforcing material adapted to immobilize the knee joint and the wrapped leg portion of the person. Strap means are provided to permit the wrapped body member to be held in position about the legs of the person. Hand restraint means are also provided along the top edge of the body member. Upright positioning of the subject (sitting or standing) is maintained by means of a shoulder harness attachable to the body member.

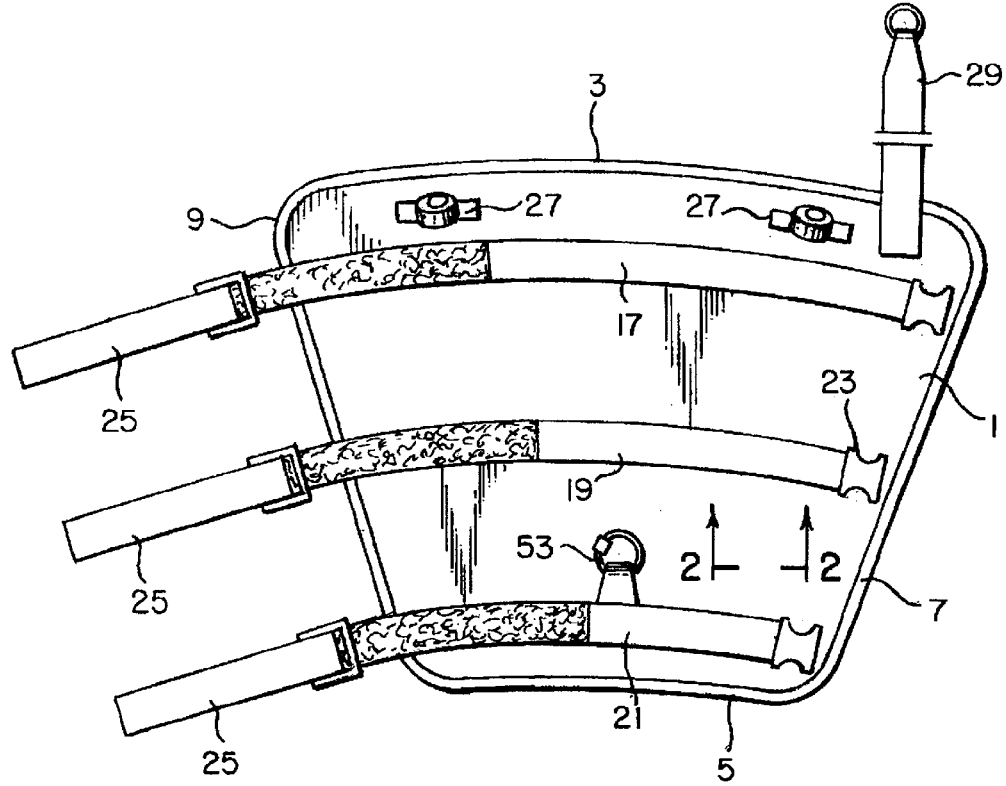

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-13 is confirmed.

* * * * *